United States Patent
Jaiswal et al.

(10) Patent No.: US 9,498,440 B2
(45) Date of Patent: Nov. 22, 2016

(54) EXTENDED RELEASE PHARMACEUTICAL COMPOSITIONS

(75) Inventors: Sunil Beharilal Jaiswal, Nagpur (IN); Vaibhavi Ankur Shah, Mumbai (IN); Sunil Deviprasad Tiwari, Maharashtra (IN)

(73) Assignee: INVENTIA HEALTHCARE PRIVATE LIMITED, Mumbai (IN)

( * ) Notice: Subject to any disclaimer, the term of this patent is extended or adjusted under 35 U.S.C. 154(b) by 140 days.

(21) Appl. No.: 13/321,154

(22) PCT Filed: May 20, 2010

(86) PCT No.: PCT/IB2010/001229
§ 371 (c)(1),
(2), (4) Date: Nov. 17, 2011

(87) PCT Pub. No.: WO2010/133961
PCT Pub. Date: Nov. 25, 2010

(65) Prior Publication Data
US 2012/0064164 A1    Mar. 15, 2012

(30) Foreign Application Priority Data
May 22, 2009   (IN) .................. 1287/MUM/2009

(51) Int. Cl.
*A61K 9/16* (2006.01)
*A61K 9/50* (2006.01)
*A61K 31/135* (2006.01)

(52) U.S. Cl.
CPC .......... *A61K 9/1652* (2013.01); *A61K 9/1694* (2013.01); *A61K 9/5073* (2013.01); *A61K 9/5078* (2013.01); *A61K 9/5084* (2013.01); *A61K 9/5089* (2013.01); *A61K 31/135* (2013.01)

(58) Field of Classification Search
None
See application file for complete search history.

(56) References Cited

U.S. PATENT DOCUMENTS

| | | | |
|---|---|---|---|
| 3,454,643 A | 7/1969 | Cope et al. | |
| 3,882,246 A | 5/1975 | Share | |
| 4,780,463 A | 10/1988 | Sunshine et al. | |
| 4,851,228 A | 7/1989 | Zentner et al. | |
| 4,968,507 A | 11/1990 | Zentner et al. | |
| 4,996,047 A | 2/1991 | Kelleher et al. | |
| 5,260,337 A | 11/1993 | Sims et al. | |
| 6,190,591 B1 | 2/2001 | Van Lengerich | |
| 6,358,944 B1 | 3/2002 | Lederman et al. | |
| 6,395,788 B1 | 5/2002 | Iglehart, III | |
| 6,569,463 B2 | 5/2003 | Patel et al. | |
| 6,923,988 B2 | 8/2005 | Patel et al. | |
| 7,387,793 B2 | 6/2008 | Venkatesh et al. | |
| 7,416,738 B2 | 8/2008 | Sowden et al. | |
| 7,544,372 B2 | 6/2009 | Venkatesh et al. | |
| 7,713,551 B2 | 5/2010 | McGurk et al. | |
| 7,790,199 B2 | 9/2010 | Venkatesh et al. | |
| 7,820,203 B2 | 10/2010 | Venkatesh et al. | |
| 7,829,121 B2 | 11/2010 | Venkatesh et al. | |
| 7,871,645 B2 | 1/2011 | Hall et al. | |
| 7,964,219 B2 | 6/2011 | Li et al. | |
| 8,029,822 B2 | 10/2011 | Faour et al. | |
| 2001/0046988 A1 | 11/2001 | Iglehart | |
| 2002/0044968 A1 | 4/2002 | Van Lengerich | |
| 2003/0064097 A1 | 4/2003 | Patel et al. | |
| 2003/0099711 A1 | 5/2003 | Meadows et al. | |
| 2003/0180352 A1* | 9/2003 | Patel et al. ................ | 424/465 |
| 2003/0180362 A1 | 9/2003 | Park et al. | |
| 2003/0211071 A1 | 11/2003 | Bologna et al. | |
| 2003/0215496 A1 | 11/2003 | Patel et al. | |
| 2003/0232083 A1 | 12/2003 | Wynn et al. | |
| 2003/0235616 A1 | 12/2003 | Sowden et al. | |
| 2004/0029869 A1 | 2/2004 | Iglehart, III | |
| 2004/0081695 A1 | 4/2004 | Sowden et al. | |
| 2004/0166160 A1 | 8/2004 | Subramanian et al. | |
| 2004/0197407 A1 | 10/2004 | Subramanian et al. | |
| 2004/0204413 A1 | 10/2004 | Faour et al. | |
| 2005/0008702 A1 | 1/2005 | Faour et al. | |
| 2005/0100594 A1* | 5/2005 | Sen et al. .................. | 424/458 |
| 2005/0106247 A1* | 5/2005 | Venkatesh et al. ........ | 424/469 |
| 2005/0265955 A1 | 12/2005 | Raman et al. | |
| 2006/0018933 A1 | 1/2006 | Vaya et al. | |
| 2006/0018934 A1 | 1/2006 | Vaya et al. | |
| 2006/0034923 A1 | 2/2006 | Li et al. | |
| 2006/0148841 A1 | 7/2006 | Lundeen | |
| 2006/0198815 A1 | 9/2006 | Barker et al. | |
| 2006/0293217 A1 | 12/2006 | Barker et al. | |
| 2007/0059270 A1 | 3/2007 | Hall et al. | |
| 2007/0140983 A1 | 6/2007 | Hall et al. | |
| 2007/0141096 A1 | 6/2007 | Van Lengerich | |
| 2007/0148239 A1 | 6/2007 | Hall et al. | |
| 2008/0124398 A1 | 5/2008 | Venkatesh et al. | |
| 2008/0124399 A1 | 5/2008 | Venkatesh et al. | |
| 2008/0287866 A1 | 11/2008 | Heller | |
| 2009/0017126 A1 | 1/2009 | Venkatesh et al. | |
| 2009/0017127 A1 | 1/2009 | Venkatesh et al. | |
| 2009/0098200 A1 | 4/2009 | Temtsin Krayz et al. | |
| 2009/0148532 A1 | 6/2009 | Venkatesh et al. | |
| 2009/0175939 A1 | 7/2009 | Bosse et al. | |
| 2009/0220611 A1 | 9/2009 | Dargelas et al. | |
| 2009/0246233 A1* | 10/2009 | Devane et al. ............. | 424/400 |
| 2009/0306204 A1 | 12/2009 | Junior et al. | |
| 2010/0034801 A1 | 2/2010 | Li et al. | |
| 2010/0098832 A1 | 4/2010 | Venkatesh et al. | |
| 2011/0076385 A1 | 3/2011 | Hall et al. | |
| 2011/0081419 A1 | 4/2011 | Hall et al. | |
| 2011/0217384 A1 | 9/2011 | Venkatesh et al. | |

FOREIGN PATENT DOCUMENTS

| | | |
|---|---|---|
| EP | 147780 | 7/1985 |
| EP | 179583 | 4/1986 |

(Continued)

Primary Examiner — Susan Tran
(74) Attorney, Agent, or Firm — Withers Bergman LLP

(57) ABSTRACT

The present invention provides extended release pharmaceutical compositions structured for once a day administration comprising skeletal muscle relaxant such as cyclobenzaprine or its pharmaceutically acceptable salt thereof that extends the release of the drug under in-vitro conditions for at least 8 to 12 hours. The invention also provides process for the preparation of such structured compositions.

16 Claims, 1 Drawing Sheet

(56) References Cited

FOREIGN PATENT DOCUMENTS

| | | |
|---|---|---|
| EP | 1849460 | 10/2007 |
| WO | WO9416703 | 8/1994 |
| WO | WO9720551 | 6/1997 |
| WO | WO9918937 | 4/1999 |
| WO | WO2006117803 | 11/2006 |
| WO | WO 2006117803 A2 * | 11/2006 |
| WO | WO2006135362 | 12/2006 |
| WO | WO2007140555 | 12/2007 |

* cited by examiner

EXTENDED RELEASE PHARMACEUTICAL COMPOSITIONS

PRIORITY

This application claims benefit of international application PCT/IB2010/001229, filed May 20, 2010, and Indian application 1287/MUM/2009, filed on May 22, 2009, the contents of all of which are incorporated by reference in their entireties herein.

FIELD OF THE INVENTION

This invention relates to extended release pharmaceutical compositions comprising skeletal muscle relaxant such as cyclobenzaprine or its pharmaceutically acceptable salt thereof and a process for preparation thereof.

BACKGROUND OF THE INVENTION

Cyclobenzaprine Hydrochloride, a skeletal muscle relaxant is currently available as immediate release tablets containing 5 mg or 10 mg of the active and also as extended release capsules containing 15 mg or 30 mg of the active. Immediate release tablets are recommended to be administered three times a day to achieve relief from muscle spasm. Administration of such tablets three times a day is a major compliance issue especially in elderly patients. To substantially enhance patient compliance, it is desirable to provide cyclobenzaprine hydrochloride in extended release dosage form for once a day administration.

U.S. Pat. No. 7,387,793, U.S. Pat. No. 7,544,372, US Patent Application 2008/0124398, US Patent Application 2009/0017126, US Patent Application 2009/0017127 and US Patent Application 20090148532 disclose multi-particulate pharmaceutical dosage forms of a skeletal muscle relaxant for once a day administration comprising a population of extended release beads. These extended release beads comprise:

an active-containing core particle comprising a skeletal muscle relaxant selected from the group consisting of cyclobenzaprine, pharmaceutically acceptable salts or derivatives thereof and mixtures thereof; and
  an extended release coating comprising a water insoluble polymer membrane surrounding the said core, wherein the membrane comprises a water insoluble polymer and a plasticizer.

The dosage form exhibits the following in-vitro dissolution profile in USP apparatus 2 (paddles @ 50 rpm) in 900 ml of 0.1N HCl at 37° C.:
  not more than 40% of the total active is released at 2 hour;
  from about 40-65% of the total active is released at 4 hour;
  from about 60-85% of the total active is released at 8 hour.

OBJECTS OF THE INVENTION

The object of the invention is to provide extended release pharmaceutical compositions structured for once a day administration comprising skeletal muscle relaxant such as cyclobenzaprine or its pharmaceutically acceptable salt thereof that exhibits in-vitro drug release profile for at least 8 to 12 hours.

It is another object of the invention to provide the said structured compositions comprising cyclobenzaprine or its pharmaceutically acceptable salt thereof, wherein the composition comprises of a core, a layer comprising of one or more extended release agents, and the said drug either in the extended release layer or in between the core and the extended release layer or in the core.

It is yet another object of the invention to provide the above compositions in the form of pellets capable of being filled in capsules.

It is yet another object of the invention to provide extended release compositions which would substantially minimize the incidence of dose dumping.

It is yet another object of the invention to provide process for the preparation of extended release pharmaceutical compositions comprising cyclobenzaprine or its pharmaceutically acceptable salts thereof that exhibits in-vitro drug release profile for at least 8 to 12 hours.

DESCRIPTION OF THE INVENTION

The present invention provides extended release pharmaceutical compositions structured for once a day administration comprising skeletal muscle relaxant such as cyclobenzaprine or it's pharmaceutically acceptable salt thereof that extends the release of the drug under in-vitro conditions for at least 8 to 12 hours.

Such structured compositions comprising skeletal muscle relaxant such as cyclobenzaprine or its pharmaceutically acceptable salt thereof comprises of:
  a) a core;
  b) a layer comprising of one or more extended release agents; and
  c) the said cyclobenzaprine or its pharmaceutically acceptable salt thereof is either (i) in the extended release layer, or (ii) in between the core and the extended release layer, or (iii) in the core.

Structuring the Composition:
In a preferred embodiment of the invention, the extended release pharmaceutical compositions comprise of:
  a) inert core;
  b) said inert core being coated with a matrix comprising cyclobenzaprine or its pharmaceutically acceptable salt thereof such as cyclobenzaprine HCl and one or more extended release agents.

In another preferred embodiment of the invention, the extended release pharmaceutical compositions comprise of:
a) inert core;
b) said inert core being coated with a matrix comprising cyclobenzaprine or its pharmaceutically acceptable salt thereof such as cyclobenzaprine HCl and one or more extended release agents and one or more plasticizer.

Figure 1A:
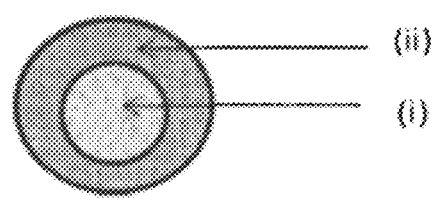
FIGS. 1(a), 1(b), and 1(c) illustrate the manner in which the compositions of the present invention can be structured.

As shown in FIG. 1(a), the composition is structured to form a matrix that comprises of an inert core (i), the inert core being coated with a layer (ii) comprising of cyclobenzaprine or its pharmaceutically acceptable salt thereof such as cyclobenzaprine hydrochloride and one or more extended release agents.

The process for the preparation of composition to obtain the structure as shown in FIG. 1(a) comprises steps of:
i. providing an inert core;
ii. applying a layer comprising of cyclobenzaprine or its pharmaceutically acceptable salt thereof such as cyclobenzaprine hydrochloride, one or more extended release agents and optionally at least one additive selected from binder, anti-tack agent, plasticizer, diluent, or mixtures thereof on the inert core to obtain extended release pellets.

Creation of the said layer on the inert core comprises steps of:
  i. dispersing and/or dissolving cyclobenzaprine or its pharmaceutically acceptable salt thereof such as cyclobenzaprine hydrochloride in a solvent selected from water, alcohol, organic solvent, or mixtures thereof to obtain drug dispersion or solution;
  ii. dispersing and or dissolving one or more extended release agents in a solvent selected from water, alcohol, organic solvent, or mixtures thereof to obtain dispersion or solution;
  iii. mixing dispersion or solution of step (ii) with drug dispersion or solution of step (i);
  iv. optionally adding at least one additive selected from binder, anti-tack agent, plasticizer, diluent, or mixtures thereof to dispersion or solution of step (iii);
  v. spraying the resulting dispersion or solution on inert cores to obtain extended release pellets;
  vi. drying and sizing the extended release pellets.

In one of the embodiments of the invention, the extended release pharmaceutical compositions comprises of:
a) inert core;
b) first layer comprising of cyclobenzaprine or its pharmaceutically acceptable salt thereof such as cyclobenzaprine HCl on the inert core; and
c) second layer comprising of one or more extended release agents on the first layer; wherein the said second layer does not contain plasticizer.

Figure 1B:
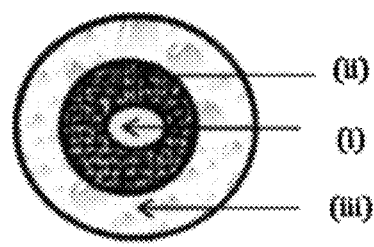

As shown in FIG. 1(b), the compositions are structured to provide an inert core (i), first layer (ii) comprising of cyclobenzaprine or its pharmaceutically acceptable salt thereof such as cyclobenzaprine hydrochloride on the inert core and second layer (iii) comprising one or more extended release agents on the first layer, wherein the said second layer does not contain plasticizer.

The process for the preparation of composition to obtain the structure as shown in FIG. 1(b) comprises steps of:
  a) providing an inert core;
  b) creating a first layer comprising of cyclobenzaprine or its pharmaceutically acceptable salt thereof such as cyclobenzaprine hydrochloride on the inert core to obtain drug core; and
  c) creating a second layer comprising of one or more extended release agents on the first layer to obtain extended release pellets;
  wherein the second layer does not contain plasticizer.

Creation of the said first layer on the inert core comprises steps of:
i. dispersing and or dissolving cyclobenzaprine or its pharmaceutically acceptable salt thereof such as cyclobenzaprine hydrochloride in a solvent selected from water, alcohol, organic solvent, or mixtures thereof to obtain drug dispersion or solution;
ii. optionally dispersing and or dissolving at least one additive selected from binder, diluent, plasticizer, anti-tack agent, or mixtures thereof in a solvent selected from water, alcohol, organic solvent, or mixtures thereof;
iii. mixing dispersion or solution of step (ii) with drug dispersion or solution of step (i);
iv. spraying the resulting dispersion or solution of step (iii) on inert cores to obtain drug cores;
v. drying and sizing the drug cores.

Creation of the second layer (extended release layer) on the drug core comprises steps of:
i. dispersing and or dissolving one or more extended release agents in a solvent selected from water, alcohol, organic solvent, or mixtures thereof to obtain dispersion or solution;
ii. optionally adding at least one additive selected from anti-tack agent, diluents, or mixtures thereof;
iii. spraying the resulting dispersion or solution on drug pellets to obtain extended release pellets;
iv. drying and sizing the extended release pellets.

In another embodiment of the invention, the extended release pharmaceutical compositions comprises of:
a) a core comprising of cyclobenzaprine or its pharmaceutically acceptable salt thereof such as cyclobenzaprine HCl;
b) a layer comprising of or more extended release agents coated on the core; wherein the said layer does not contain plasticizer.

Figure 1C:
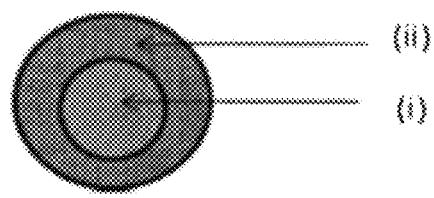

As shown in FIG. 1(c), the compositions are structured to form a core (i) comprising of cyclobenzaprine or its pharmaceutically acceptable salt thereof such as cyclobenzaprine hydrochloride, the core being coated with a layer (ii) comprising of one or more extended release agents, wherein the said coating layer does not contain plasticizer.

The process for the preparation of the compositions as shown in FIG. 1(c) comprises steps of:
i. providing a matrix core comprising of cyclobenzaprine or its pharmaceutically acceptable salt thereof such as cyclobenzaprine hydrochloride and at least one additive selected from binder, anti-tack agent, plasticizers, diluents, or mixtures thereof;
ii. creating a layer comprising of one or more extended release agents on the matrix core to obtain extended release pellets, the layer optionally comprises of at least one additive selected from anti-tack agent, diluents, or mixtures thereof, wherein the said layer does not contain plasticizer.

Preparation of the said matrix core comprises steps of:
i. mixing cyclobenzaprine or its pharmaceutically acceptable salt thereof such as cyclobenzaprine hydrochloride with at least one additive selected from binder, anti-tack agent, plasticizers, diluents, or mixtures thereof in a mixer to obtain drug mixture;
ii. granulating drug mixture with a granulating solvent selected from water, alcohol, organic solvent, or mixtures thereof to obtain the granules;
iii. extruding the granules in an extruder to obtain the extrudates;
iv. spheronizing the extrudates in the spheronizer to obtain the matrix core;
v. drying and sizing the matrix core.

Creation of the said extended release layer on the said matrix core comprises steps of:
i. dispersing and or dissolving one or more extended release agents in a solvent selected from water, alcohol, organic solvent, or mixtures thereof to obtain dispersion or solution;
ii. optionally adding at least one additive selected from anti-tack agent, diluents, or mixtures thereof;
iii. spraying the resulting dispersion or solution on the matrix cores to obtain extended release pellets;
iv. drying and sizing the extended release pellets.

Cyclobenzaprine salt is the addition salt of cyclobenzaprine with an inorganic acid such as hydrochloric, hydrobromic, phosphoric, nitric, or sulphuric or of organic acid such as tartaric, acetic, propionic, hydroxyacetic, oxaloacetic, oxalic, pyruvic, succinic, malic, malonic, fumaric, lactic, glutaric, maleic, sulphonic, benzenesulphonic, and the like.

The preferred cyclobenzaprine salt is cyclobenzaprine HCl and is usually administered in the dose of 15 mg and 30 mg strength.

There is no limitation on the particle sizes of cyclobenzaprine HCl used in the invention. However, the particle size of cyclobenzaprine HCl ranges from 0.1 microns to 1000 microns, preferably from 0.5 micron to 500 microns, more preferably from 1 micron to 200 microns and most preferably from 2 microns to 100 microns.

Cyclobenzaprine HCl in the composition is from 0.01% to 50% by weight, preferably from 0.05% to 40%, more preferably from 0.1% to 25%, and most preferably from 2.5% to 15% by weight of the composition.

Extended release agent is selected from the group of cellulose ethers, cellulose esters polymethacrylates, wax, fatty acid, fatty alcohol, polyalkylene glycol, or mixtures thereof. However, any other suitable agent(s) that extends the release of cyclobenzaprine HCl from the dosage form may also be used.

Representative examples of such agent includes ethylcellulose powder, aqueous dispersion of ethylcellulose (such as SURELEASE®, AQUACOAT® ECD 30) hydroxypropylcellulose, hydroxypropylmethylcellulose, hydroxyethylcellulose, carboxymethylcellulose, sodium carboxymethylcellulose, calcium carboxymethylcellulose, methylcellulose, cellulose acetate phthalate, hydroxypropylmethylcellulose phthalate, hydroxypropylmethylcellulose acetate succinate, cellulose acetate butyrate, cellulose acetate trimellitate, cellulose acetate, polyvinyl alcohol, polyvinyl acetate (such as KOLLICOAT SR 30D), povidone, polyethylene glycol, cetyl alcohol, stearyl alcohol, bees wax, carnauba wax, stearic acid, vinyl pyrrolidone-vinyl acetate copolymer (such as KOLLIDON VA 64, KOLLIDON SR), dimethylaminoethyl methacrylate and other neutral methacrylic acid esters (such as Eudragit E), methacrylic acid copolymers type A (such as Eudragit L), methacrylic acid copolymers type B (such as Eudragit S), methacrylic acid copolymers type C (such as Eudragit L 30D 55), ammoniomethacrylate copolymers (such as Eudragit RL, Eudragit RS), neutral copolymer of polymethacrylic acid ester (Such as Eudragit NE 30D), or mixtures thereof.

Mixtures of extended release agents are generally used in the ratio of 1:0.05 to 0.05:1, preferably in the ratio of 1:0.15 to 0.15:1, more preferably in the ratio of 1:0.3 to 0.3:1, and most preferably in the ratio of 1:0.5 to 0.5:1.

These extended release agents, in general, are available in various viscosity grades. For example hydroxypropylmethylcellulose is available in viscosity grade of 5 cps, 6 cps, 15 cps, 100 cps, 4000 cps, 15000 cps and 100000 cps. Similarly, ethyl cellulose powder is available in viscosity grade of 3 cps, 5 cps, 7 cps, 10 cps, 20 cps, 45 cps, 50 cps and 100 cps. Such agents may be used alone or in mixture i.e. mixture of two or more different viscosity grade. For example, extended release layer may comprise of mixture of ethyl cellulose (10 cps) and ethyl cellulose (45 cps). Such mixtures are generally used in the ratio of 1:0.05 to 0.05:1, preferably in the ratio of 1:0.15 to 0.15:1, more preferably in the ratio of 1:0.3 to 0.3:1, and most preferably in the ratio of 1:0.5 to 0.5:1.

The extended release agent in the composition is from 0.5% to 90% by weight, preferably from 1% to 75%, more preferably from 2.5% to 60%, most preferably from 5% to 50% by weight of the composition.

The extended release agent in the composition is from about 50% to about 90% by weight of the matrix, preferably from about 65% to about 85% by weight of the matrix Plasticizer is selected from the group of triacetin, triethylcitrate, tributyl citrate, polyethylene glycol, acetyltributylcitrate, miglyol, hydrogenated oils, propylene glycol, acetyltriethylcitrate, polysorbate, castor oil, oleic acid, dibutylsebacate, diethylphthalate, acetylated mono- and di-glycerides, or mixtures thereof.

Plasticizer in the composition is from 0.1% to 30% by weight, preferably from 0.5% to 20%, more preferably from 1% to 10%, and most preferably from 1.5% to 5% by weight of the composition.

The inert core used in the composition is non-pareil seeds or sugar sphere or any other suitable inert material. Examples of such material include sugar, starch, cellulose, microcrystalline cellulose, resin, glass beads, or mixtures thereof. The average particle size of inert core in the present invention is from about 150 microns to about 2000 microns, preferably from about 250 microns to about 1000 microns, more preferably from about 350 microns to about 850 microns, and most preferably from about 500 microns to about 600 microns.

Inert core in the composition is from 15% to 80% by weight, preferably from 25% to 75%, more preferably from 30% to 60%, and most preferably from 40% to 50% by weight of the composition.

Diluent is selected from microcrystalline cellulose, starch, pregelatinized starch, starch 1500, cellulose, sucrose, lactose, glucose, dextrose, mannitol, sugar, cross linked povidone, sodium starch glycolate, croscarmellose sodium, croscarmellose potassium, croscarmellose calcium, monobasic sodium phosphate, dibasic sodium phosphate, tribasic sodium phosphate, calcium phosphate, dibasic calcium phosphate, tribasic calcium phosphate, calcium sulfate, calcium carbonate, or mixtures thereof Diluent in the composition is from 5% to 95% by weight, preferably from 20% to 90%, more preferably from 35% to 80%, most preferably from 50% to 70% by weight of the composition.

Binder is selected from xanthan gum, guar gum, acacia, tragacanth, gelatin, carrageenan polyvinylpyrrolidone, carbomer, locust bean gum, karaya gum, copovidone, agar, hydroxypropylmethylcellulose, hydroxypropylcellulose, hydroxyethylcellulose, polyethylene oxide, sodium carboxymethylcellulose, chitosan, sodium alginate, or mixtures thereof.

Binder in the composition is from 0.1% to 30% by weight, preferably from 0.5% to 20%, more preferably from 1% to 10%, and most preferably from 1.5% to 5% by weight of the composition.

Anti-tack agent is selected from talc, colloidal silicon dioxide, glyceryl monostearate, sodium benzoate, sodium lauryl sulfate, waxes, glyceryl behenate, stearic acid, magnesium stearate, calcium stearate, sodium stearyl fumarate, or mixtures thereof.

Anti-tack agent in the composition is from 0.1% to 30% by weight, preferably from 0.5% to 20%, more preferably from 1% to 10%, and most preferably from 1.5% to 5% by weight of the composition.

The solvent is selected from water, alcohol, organic solvent, or mixtures thereof. Examples of such solvent include methanol, ethanol, isopropanol, dichloromethane, acetone, halogenated hydrocarbon, ethylmethylketone, or mixtures thereof.

The pharmaceutical composition of the present invention comprises of Cyclobenzaprine or its pharmaceutically acceptable salt thereof such as Cyclobenzaprine HCl and one or more agents for extended release that exhibits in-vitro drug release for at least 8 to 12 hours.

Extended release compositions comprising Cyclobenzaprine hydrochloride when analyzed in-vitro in USP apparatus 2, in 0.1N HCl exhibits in-vitro dissolution profile of:
at least 5% of cyclobenzaprine HCl at $1^{st}$ hour;
at least 30% of cyclobenzaprine HCl at $4^{th}$ hour;
at least 50% of cyclobenzaprine HCl at $8^{th}$ hour;
at least 60% of cyclobenzaprine HCl at $16^{th}$ hour.

Preferably, extended release compositions comprising Cyclobenzaprine hydrochloride when analyzed in-vitro in USP apparatus 2, in 0.1N HCl exhibits in-vitro dissolution profile of:
from 5% to 50% of cyclobenzaprine HCl at $1^{st}$ hour;
from 30% to 80% of cyclobenzaprine HCl at $4^{th}$ hour;
from 50% to 100% of cyclobenzaprine HCl at $8^{th}$ hour;
at least 75% of cyclobenzaprine HCl at $16^{th}$ hour.

Extended release pellets comprising cyclobenzaprine HCl complying with the desired dissolution profile are filled in empty hard gelatin capsule to delivery therapeutic effective amount of cyclobenzaprine HCl.

The invention further provides non-limiting examples.

EXAMPLE 1

Preparation of Extended Release Pellets a) Cyclobenzaprine HCl (30 g) was dissolved in purified water (100 g) to obtain drug solution;
b) Eudragit L 100 (75 g) was dissolved in the mixture of acetone (300 g) and water (30 g);
c) Eudragit RSPO (75 g) was dissolved in acetone (160 g);
d) The solutions obtained in step a, step (b), and step (c) were mixed and the resulting solution was sprayed on was sprayed on inert core (20-25 mesh ASTM) (150 g) in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain extended release pellets;
e) Extended release pellets were dried in fluid bed bottom spray processor to arrive at the moisture content of less than 5% w/w, preferably less than 3% w/w, and more preferably less than 2% w/w;
f) The dried pellets were sized, optionally lubricated with purified talc and were filled in empty hard gelatin capsule.

EXAMPLE 2

Preparation of Extended Release Pellets a) Cyclobenzaprine HCl (30 g) was dissolved in purified water to obtain drug solution;
b) Polyethylene glycol 6000 (8 g) was added to the drug solution of step a) and stirred to obtain clear solution;
c) Ethyl cellulose (45 cps) (67.5 g) was dispersed in water to obtain dispersion;
d) Isopropanol was added to dispersion of step (c) and stirred to obtain clear solution;
e) Kollidon SR (15 g) was added to the solution of step (d) and stirred to obtain clear solution;
f) The solution obtained in step (b) was mixed with the solution obtained in step (e) and the resulting solution was sprayed on sugar sphere (30-35 mesh ASTM) (80 g) in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain extended release pellets;
g) Extended release pellets were dried in fluid bed bottom spray processor to arrive at the moisture content of less than 5% w/w, preferably less than 3% w/w, and more preferably less than 2% w/w;
h) The dried pellets were sized, lubricated with purified talc (1.5 g) and were filled in empty hard gelatin capsule.

EXAMPLE 3

Preparation of Extended Release Pellets a) Cyclobenzaprine HCl (30 g) was dissolved in purified water to obtain drug solution;
b) Ethyl cellulose (10 cps) (67.5 g) and ethyl cellulose (45 cps) (15 g) were added to the drug solution of step (a) to obtain dispersion;
c) Isopropanol was added to the dispersion of step (b) and stirred to obtain clear solution;
d) Diethyl phthalate (4 g) was added to the solution of step (c) and the resulting solution was sprayed on inert core (40-60 mesh ASTM) (123.5 g) in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain extended release pellets;
e) Extended release pellets were dried in fluid bed bottom spray processor to arrive at the moisture content of less than 5% w/w, preferably less than 3% w/w, and more preferably less than 2% w/w;
f) The dried pellets were sized, lubricated with purified talc and were filled in empty hard gelatin capsule.

EXAMPLE 4

Preparation of Matrix Cores a) Cyclobenzaprine HCl (30 mg/unit), microcrystalline cellulose pH 101 (100 mg/unit) glyceryl monostearate (50 mg/unit) and Kollidon SR (50 mg) were mixed to obtain drug mixture;
b) Drug mixture was granulated with the solution of sodium carboxymethylcellulose 7MF (2 mg) in water to obtain granules.
c) The granules were extruded and spheronized to obtain matrix core.
d) The matrix cores were dried and sized.

EXAMPLE 5

Preparation of Drug Cores a) Cyclobenzaprine hydrochloride (30 mg/unit) was dissolved in the mixture of water and isopropanol.
b) Colloidal silicon dioxide (6.02 mg/unit) and iron oxide yellow (0.19 mg/unit) were added to the above solution to obtain dispersion;
c) The dispersion was sprayed on inert cores (116.27 mg/unit) (18-20 mesh ASTM) in fluid bed bottom spray processor with inlet air temperature of about 20° C. to about 80° C., outlet air temperature of about 20° C. to about 60° C., atomization air pressure of about 0.5-3.5 bars, fluidization flap open from about 10% to about 90% w/w to obtain drug cores.
d) The resulting drug cores were dried and sized.

EXAMPLE 6

Preparation of Extended Release Pellets

The matrix cores of example 4 or the drug cores of example 5 were coated with extended release layer comprising ethyl cellulose 10 cps (4.7% by weight of the composition) to obtain extended release pellets. These extended release pellets were dried sized lubricated and filled in capsule.

Extended release compositions comprising cyclobenzaprine hydrochloride (examples 1 to 6) when analyzed in-vitro in USP apparatus 2, in 0.1N HCl (900 ml) exhibits in-vitro dissolution profile of:

from 10% to 38% of cyclobenzaprine HCl at $1^{st}$ hour;
from 33% to 68% of cyclobenzaprine HCl at $4^{th}$ hour;
from 68% to 81% of cyclobenzaprine HCl at $8^{th}$ hour;
from 79 to 88% of cyclobenzaprine HCl at $16^{th}$ hour.

STATEMENT OF PREFERRED EMBODIMENTS OF THE INVENTION

While the invention has been described with respect to preferred embodiments, those skilled in the art will readily appreciate that various changes and/or modifications can be made to the invention without departing from the spirit or scope of the invention as defined by the appended claims.

We claim:

1. An extended release pellet composition for oral administration comprising:
    a. an inert core;
    b. said inert core being coated with a matrix coat by spraying a dispersion or solution consisting essentially of cyclobenzaprine or a pharmaceutically acceptable salt thereof and two or more extended release agents, wherein the two or more extended release agents comprise ethyl cellulose, hydroxypropyl methylcellulose phthalate, hydroxypropyl methylcellulose acetate succinate, cellulose acetate, polyvinyl alcohol, polyvinyl acetate, cetyl alcohol, stearyl alcohol, bees wax, carnauba wax, stearic acid, vinyl pyrrolidone-vinyl acetate copolymer, dimethylaminoethyl methacrylate and other neutral methacrylic acid esters, methacrylic acid copolymers type A, methacrylic acid copolymers type B, methacrylic acid copolymers type C, ammoniomethacrylate copolymers, neutral copolymer of polymethacrylic acid ester, or mixtures thereof, from about 50% to about 90% by weight of the said matrix; said matrix comprising from about 35% to about 85% by weight of the extended release composition; and,
    c. wherein the viscosity of the two or more extended release agents is in the range of 3 cps to 50 cps: and,
    d. wherein the ratio of cyclobenzaprine or a pharmaceutically acceptable salt thereof, and the two or more extended release agents, in the said matrix, is in the range of 1:2.8 to 1:5; and,
    e. wherein the extended release pellet composition is encapsulated in a hard gelatin capsule.

2. The composition as claimed in claim 1, wherein the two or more extended release agents comprise about 65% to about 85% by weight of the matrix.

3. The composition as claimed in claim 1, comprising cyclobenzaprine or a pharmaceutically acceptable salt thereof from 0.01% to 50% by weight of the composition.

4. A process for the preparation of extended release pharmaceutical composition of claim 1, wherein the process comprises steps of:
    a. dispersing and/or dissolving cyclobenzaprine or a pharmaceutically acceptable salt thereof in a solvent comprising water, alcohol, organic solvent, or a mixture thereof;
    b. dispersing and/or dissolving two or more extended release agents in a solvent comprising water, alcohol, organic solvent, or a mixture thereof;
    c. mixing the dispersion or solution of step b) with the dispersion or solution of step a);
    d. optionally adding at least one additive comprising a binder, diluent, surfactant, plasticizer, anti-tack agent, lubricants, or a mixture thereof to dispersion of step c);
    e. spraying the resulting dispersion or solution, as a matrix, on inert cores to obtain extended release pellets, wherein the extended release agent(s) is 50% to 90% by weight of said matrix,
    f. drying and sizing the extended release pellets; and,
    g. filling the extended release pellets into a hard gelatin capsule.

5. A method of relieving muscle spasm in a patient in need thereof, comprising orally administering to the patient the extended release composition of claim 1.

6. The composition as claimed in claim 1 wherein the pharmaceutically acceptable cyclobenzaprine salt is cyclobenzaprine hydrochloride.

7. The composition as claimed in claim 1 wherein the extended release agents are a mixture of the agents selected from the group consisting of methacrylic acid copolymers type A, methacrylic acid copolymers type B, methacrylic acid copolymers type C, hydroxypropyl methylcellulose phthalate, hydroxypropyl methylcellulose acetate succinate, vinyl pyrrolidone-vinyl acetate copolymer, ethylcellulose and cetyl alcohol.

8. The composition as claimed in claim 1 wherein the extended release composition when analyzed in-vitro in 0.1N hydrochloric acid using USP apparatus 2 (900 mL, 37° C.), exhibits a dissolution of 5% to 50% of cyclobenzaprine or a pharmaceutically acceptable salt thereof, at 1 hour.

9. The composition as claimed in claim 5 wherein the pharmaceutically acceptable cyclobenzaprine salt is cyclobenzaprine hydrochloride.

10. An extended release pellet composition comprising:
    a. an inert core;
    b. said inert core, comprising from about 40% to about 52% ww of the extended release composition, is coated with a matrix coat by spraying a dispersion or solution comprising cyclobenzaprine hydrochloride and two or more extended release agents selected from ethyl cellulose, hydroxypropyl methylcellulose phthalate, hydroxypropyl methylcellulose acetate succinate, cellulose acetate, cetyl alcohol, vinyl pyrrolidone-vinyl acetate copolymer, methacrylic acid copolymers type A, methacrylic acid copolymers type B, methacrylic acid copolymers type C, ammoniomethacrylate copolymers, neutral copolymer of polymethacrylic acid esters, or mixtures thereof;
    c. wherein the viscosity of the two or more extended release agents is in the range of 3 cps to 50 cps; and,
    d. wherein the ratio of cyclobenzaprine hydrochloride and the two or more extended release agents, in the said matrix, is in the range of 1:2.8 to 1:5; and,
    e. wherein cyclobenzaprine hydrochloride comprises from about 9% to about 15% w/w of the composition and the said extended release agents comprise from about 34% to about 45% w/w of the extended release composition; and f. wherein the extended release pellet composition is encapsulated in a hard gelatin capsule; and, g. the capsule form when analyzed in-vitro in 0.1N hydrochloric acid using USP apparatus 2 (900 mL, 37° C.), exhibits a dissolution of 10% to 38% of cyclobenzaprine hydrochloride at 1 hour.

11. The compositions as claimed in claim 10, wherein the matrix further. comprises one or more plasticizer.

12. The composition as claimed in claim 11, the plasticizer is selected from triacetin, triethylcitrate, tributyl citrate, polyethylene glycol, acetyltribytylcitrate, miglyol, hydrogenated oils, propylene glycol, acetyltriethylcitrate, polysorbate, castor oil, oleic acid, dibutylsebacate, diethylphthalate, acetylated mono- and di-glycerides, or mixtures thereof.

13. The composition as claimed in claim 10, wherein the composition further comprises at least one pharmaceutically acceptable additive comprising a binder, diluent, anti-tack agent, or mixtures thereof.

14. The extended release composition of claim 10
   a. wherein the inert core comprises about 45% (w/w) of the extended release composition and is coated with a matrix comprising cyclobenzaprine hydrochloride Eudragit L, and Eudragit RSPO;
   b. wherein cyclobenzaprine hydrochloride comprises about 9% (w/w) of the composition and the extended release agents Eudragit L and Eudragit RSPO each comprise about 23% (w/w) of the extended release composition.

15. An extended release pellet composition for oral administration comprising:
   a. an inert core;
   b. said inert core being coated with a matrix coat consisting essentially of cyclobenzaprine or a pharmaceutically acceptable salt thereof and two or more extended release agents, wherein the two or more extended release agents comprise ethyl cellulose, hydroxypropyl methylcellulose phthalate, hydroxypropyl methylcellulose acetate succinate, cellulose acetate, polyvinyl alcohol, polyvinyl acetate, cetyl alcohol, stearyl alcohol, bees wax, carnauba wax, stearic acid, vinyl pyrrolidone-vinyl acetate copolymer, dimethylaminoethyl methacrylate and other neutral methacrylic acid esters, methacrylic acid copolymers type A, methacrylic acid copolymers type B, methacrylic acid copolymers type C, ammoniomethacrylate copolymers, neutral copolymer of polymethacrylic acid ester, or mixtures thereof, from about 50% to about 90% by weight of the said matrix;
   said matrix comprising from about 35% to about 85% by weight of the extended release composition;
   wherein the ratio of cyclobenzaprine or a pharmaceutically acceptable salt thereof and the two or more extended release agents, in the said matrix, is in the range of 1:2.8 to 1:5; and,
   c. wherein the extended release pellet composition is encapsulated in a hard gelatin capsule.

16. The composition as claimed in claim 15 wherein the pharmaceutically acceptable cyclobenzaprine salt is cyclobenzaprine hydrochloride.

* * * * *